United States Patent [19]

Pearce

[11] Patent Number: 5,204,373
[45] Date of Patent: Apr. 20, 1993

[54] FARNESYLATED TETRAHYDRO-NAPHTHALENOLS AS HYPOLIPIDEMIC AGENTS

[75] Inventor: Bradley C. Pearce, East Hampton, Conn.

[73] Assignee: Bristol-Myers Squibb Company, New York, N.Y.

[21] Appl. No.: 749,778

[22] Filed: Aug. 26, 1991

[51] Int. Cl.$^5$ .................. A61K 31/08; C07C 43/21; C07C 43/23
[52] U.S. Cl. .................. 514/720; 514/732; 568/632; 568/633; 568/634
[58] Field of Search .................. 568/632, 633, 634; 514/720, 732

[56] References Cited

U.S. PATENT DOCUMENTS 4,603,142 7/1986 Burger et al.
4,680,310 7/1987 Hengartner et al. ............. 568/632
4,935,560 6/1990 Klaus et al. ............. 568/632

OTHER PUBLICATIONS

Expert Panel "Report on the National Cholesterol Education Program Expert Panel on Detection, Evaluation and the Treatment of High Blood Cholesterol in Adults," *Arch.Intern.Med.* 148, 36–39, (1988).
Brown, et al., *J. Lipid Res*, 21: 505–517 (1980).
Wright, et al, *A symposium On Drugs Affecting Lipid Metabolism*, Houston, Tex. (Nov. 1989).
Qureshi, et al, *J. Biol. Chem.* 261: 10544–10550, (1986).
Qureshi, et al, *Suppression of Cholesterolgenesis in Hypercholesterolemic Humans by Tocotrienols of Barley and Palm Oils*, Antioxidant and Degenerative Diseases Conference, Berkeley, Calif. (Jan. 1990).
Yamaoka, et al, *Yukagaku*, 34: 120–122 (1985).
Santrucek, M., Krepelka, J., *Drugs of the Future*, 13: 973–996 (1988).
Buckley, M., Goa, K. L., Price, A. H., Brogden, R. N., *Drugs*, 37: 761–800 (1989).
Gwynne, J. T., Schwartz, C. J., *Am. J. Cardiology*, 62: 1B–77B (1988).

*Primary Examiner*—Marianne M. Cintins
*Assistant Examiner*—John Peabody
*Attorney, Agent, or Firm*—Michelle A. Kaye

[57] ABSTRACT

The invention relates to novel farnesylated tetrahydro-naphthalenols, that inhibit HMGR activity which results in a decrease in serum total cholesterol, a decrease in LDL cholesterol levels, and inhibition of LDL oxidation. The farnesylated tetrahydro-naphthalenols of the present invention are thus useful for cholesterol/lipid lowering in cases of hypercholesterolemia, hyperlipidemia, and atherosclerosis.

9 Claims, No Drawings

FARNESYLATED TETRAHYDRO-NAPHTHALENOLS AS HYPOLIPIDEMIC AGENTS

BACKGROUND OF THE INVENTION

1. Field of the Invention

The present invention relates to new farnesylated tetrahydro-naphthalenols, which are useful for cholesterol/lipid lowering in cases of hypercholesterolemia, hyperlipidemia, and atherosclerosis. Also provided are pharmaceutical compositions and a method of use employing those compositions.

2. Description of the Prior Art

It is generally recognized that high blood cholesterol levels are a significant risk factor in cardiovascular disease. Studies have demonstrated that with very few exceptions, populations which consume large quantities of saturated fat and cholesterol have relatively high concentrations of serum cholesterol and high mortality rate from coronary heart disease. (The Expert Panel "Report of the National Cholesterol Education Program Expert Panel on Detection, Evaluation, and the Treatment of High Blood Cholesterol in Adults," *Arch. Intern. Med.* 148, 36–39, (1988)).

It has been established that 3-hydroxy-3-methylglutaryl coenzyme A reductase (HMGR) is the first rate limiting enzyme in the biosynthetic pathway for cholesterol, that inhibition of HMGR activity results in a decrease in serum total cholesterol and LDL cholesterol levels, and that a decrease in serum LDL-cholesterol levels is reflected in a reduction of plasma level of apolipoprotein B. (Brown, et al, *J. Lipid Res,* 21: 505–517 (1980)).

Tocotrienols have been shown to suppress HMGR resulting in the inhibition of cholesterol biosynthesis and a subsequent drop in LDL cholesterol, apolipoprotein B, thromboxane $B_2$, platelet factor 4 and glucose levels. (Wright, et al, *A Symposium On Drugs Affecting Lipid Metabolism,* Houston, Tex. (November 1989)). In *J. Biol. Chem,* 261: 10544–10550, (1986), Qureshi, et al. indicated that the hypocholesterolemic effects of alpha-tocotrienol is brought about by the suppression of HMGR as measured by hepatic HMGR activity. (Qureshi, et al, *J. Biol. Chem,* 261: 10544–10550, (1986)). Wright et al, supra, showed that tocotrienol-rich fraction (TRF) fed to hypercholesterolemic swine resulted in a dramatic decrease in serum total cholesterol and LDL-cholesterol levels. Qureshi, et al, showed that gamma and delta-tocotrienols suppress HMGR activity. (Qureshi, et al, *Suppression of Cholesterolgenesis in Hypercholesterolemic Humans by Tocotrienols of Barley and Palm Oils,* presented at the Antioxidant and Degenerative Diseases Conference, Berkeley, Calif., (January, 1990)). U.S. Pat. No. 4,603,142 to Qureshi et al., (1986) discloses the use of alpha-tocotrienol for the lowering of lipids.

The tocotrienols are structurally related to the tocopherols (vitamin E) and differ only by possessing unsaturation in the isoprenoid side chain. Like the tocopherols, the tocotrienols have antioxidative activity, (Yamaoka, et al, *Yukagaku,* 34: 120–122 (1985)). Active oxygen species are known to play pivotal roles in the genesis of atherosclerotic plaques, thrombotic episodes, ischemic damage, cancer, aging, dementia, and inflammatory conditions. (Sies, H., *Oxidative Stress;* Academic Press, New York, (1985); Santrucek, M., Krepelka, J., *Drugs of the Future,* 13: 973–996 (1988)). Of particular interests are the potential protective effects of antioxidants on lipoproteins, since oxidized LDL is thought to be atherogenic. (Buckley, M., Goa, K. L., Price, A. H., Brogden, R. N., *Drugs.* 37: 761–800 (1989); Gwynne, J. T., Schwartz, C. J., *Am. J. Cardiology,* 62: 1B–77B (1988)). The antioxidative activity of the tocotrienols may be of value in conjunction with their hypolipidemic properties.

A possible liability with the tocotrienols is metabolism of the highly electron-rich benzopyran nucleus. This could lead to oxidative opening of the pyran ring, additional ring hyroxylation and finally excretion via bioconjugation reactions. Our objective was to find analogues possessing greater metabolic stability. The carba-tocotrienol analogs were found to exhibit enhanced lipid lowering activity relative to the tocotrienols as measured in vivo.

The present invention describes the synthesis and preliminary biological evaluation of new farnesylated tetrahydro-naphthalenols analogs.

SUMMARY OF THE INVENTION

The present invention provides farnesylated tetrahydro-naphthalenols which are useful for cholesterol/lipid lowering in cases of hypercholesteremia, hyperlipidemia and atherosclerosis.

Also provided are prodrugs of the compounds of the present invention.

In an embodiment, the present invention provides a pharmaceutical composition which comprises at least one compound of the present invention and a non-toxic pharmaceutically acceptable carrier.

In another embodiment, the present invention provides a method of treating hypercholesteremia, hyperlipidemia and thromboembolic disorders in birds and mammals, including humans, which consists of administering at least one compound of the present invention to a host in need of such treatment.

In yet another embodiment, the present invention provides a method of inhibiting LDL oxidation in birds and mammals, including humans, which consists of administering at least one compound of the present invention to a bird or mammal in need of such treatment.

In a further embodiment, the present invention provides a method of making the compounds of the present invention.

These and other advantages and objects of the invention will be apparent to those skilled in the art.

DETAILED DESCRIPTION OF THE INVENTION

The present invention provides tetrahydronaphthalenols of the Formula (I)

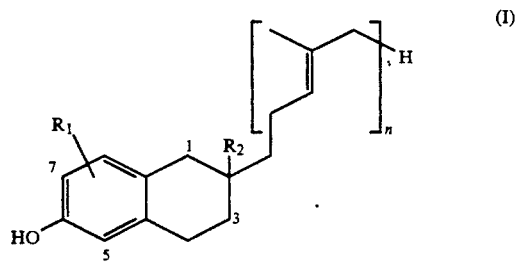

wherein $R_1$ represents hydrogen, $C_1$–$C_{10}$ lower alkyl, halogen, or OMe;

$R_2$ represents hydrogen, $C_1$–$C_{10}$ lower alkyl; and n is 1–3, preferably 3.

The present invention also provides prodrugs of the compounds of Formula I which prodrugs have the general formula II

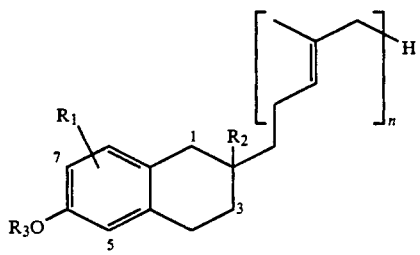

wherein $R_3$ is a physiologically hydrolyzable ester, preferably an ester of phenol such as acetate, nicotinate or succinate; and $R_1$, $R_2$, and n are as described in Formula I.

Due to the carbon double bond at the 3'-position, the compounds of Formulas I and II exist as geometric isomers having either the E- or Z-configuration, and the invention includes both isomers and mixtures thereof. The R-isomer, the S-isomer and the racemic mixture (at the C-2 position) are also included within the scope of the compounds of Formulas I and II.

Also included within the scope of the present invention are the pharmaceutically acceptable acid addition salts, the metal salts and the solvates of the compounds of Formulas I and II which may exist in various tautomeric forms.

The term "$C_1$–$C_{10}$ lower alkyl" as used herein and in the claims (unless the context indicates otherwise) mean branched or straight chain alkyl groups having 1 to 10 carbon atoms such as methyl, ethyl, propyl, isopropyl, butyl, isobutyl, t-butyl, etc., preferably one atom. The term "halogen" as used herein and in the claims (unless otherwise specified in the particular instance) is intended to include chloride, bromide, fluoride, and iodide.

The term "prodrug" as used herein and in the claims (unless the context indicates otherwise) denotes an analog of an active drug which is converted after administration back to the active drug. More particularly, it refers to analogs of tetrahydro naphthanlenols which are capable of undergoing hydrolysis of the ester moiety or oxidative cleavage of the ester moiety so as to release active, free drug. The physiologically hydrolyzable esters serve as prodrugs by being hydrolyzed in the body to yield the parent drug per se.

Synthesis of Farnesylated Naphthalenols

Synthesis of the naphthalenols 7 and 12 is outlined in schemes I and II and begins with the known tetralone 1 (Kieboom et al. *Synthesis*, 476–478 (1970)). The known hydroxymethylene derivative 2 [ibid] is prepared in a modified procedure using potassium t-butoxide in toluene at −78° in high yield. Reduction of both carbonyl groups proceeds smoothly using borane (Lau et al., *J. Org. Chem.*, 54: 491 (1989)) to give alcohol 3. Activation of the alcohol required conversion the reactive trifluoromethanesulfonate ester. With the triflate 4 in hand, homologation was straightforward using the coupling methodology of Inomata et al., *Chem. Letters,* 1177 (1986). In this case (E),(E)-farnesyl p-tolysulfone (Greico et al., *J. Org. Chem.*, 39: 2135 (1974)) was metalated with n-butyllithium and alkylated with the triflate 4. Reductive cleavage of the sulfone 5 occurs stereospecifically and regiospecifically with Pd(II) and super hydride (Inomata et al., *Chem. Letters,* 1177 (1986)) to give the farnesylated compound 6. Removal of the methyl ether was done using a modification of the procedure of Keinan et al., (*Pure & Appl. Chem.* 60: 89 (1988)) in which para-aminothiophenol serves as a nucleophilic reagent for dealkylation. This process occurs cleanly and yields the phenol 7 as indicated in scheme I.

The synthesis of naphthalenol 12 begins with the known tetralone 8 (Kieboom et al., *Synthesis* 476–478 (1970)). This compound undergoes smooth demethylation with pyridine hydrochloride at 220° to give the known phenol 9 (Buchta et al., *Ann.* 576: 7–19 (1952)). The phenol was protected as its t-butyldimethylsilyl ether 10 and was metalated using lithium diisopropyl amide. The enolate was coupled with homofarnesyl iodide to give the ketone 11 in modest yield. Removal of the ketone to the methylene oxidation state was done stepwise. Treatment of the ketone 11 with lithium aluminum hydride gave an excellent yield of the intermediate alcohols. Reductive cleavage of the benzylic alcohols using lithium metal in ammonia, required activation by acetylation [failure to do this resulted in reduction of the aromatic ring]. This two step reduction procedure provided the naphthalenol 12 in good yield as shown in scheme II.

Biological Data

The biological activity of the compounds of Formula I may be demonstrated in the following biological tests.

β-Hydroxy-β-Methylglutaryl Coenzyme A Reductase (HMGR) activity in the liver of drug dosed chickens.

Serum cholesterol, triglycerides, low density and high density liproprotein cholesterol as determined in drug treated birds.

Inhibition of LDL oxidation as measured by conjugated diene formation.

Ex Vivo HMGR Suppression and In Vivo Biological Evaluation in Normocholesterolemic Chickens Newborn male chicks (8 for each group) were raised on a standard corn-soybean based control diet for two weeks and then switched to either control or experimental diets for four weeks. Drug treatment consisted of the addition of test compounds to the corn-soybean-based diet at a concentration of 50 ppm. At the end of the feeding period, all the birds were fasted (36 hours) and refed (48 hours) to induce cholesterolgenic enzymes prior to sacrifice. The specific activity of HMGR, total serum cholesterol levels, LDL cholesterol and HDL cholesterol pools were determined using previously described methods (Qureshi et al., *J. Biol. Chem.*, 261, 10544 (1986)) (Table 1).

TABLE 1

| | Effects of test compound and tocotrienol on Lipid Metabolism in 6-week old male chickens | | | |
|---|---|---|---|---|
| Compound | Total Cholesterol | LDL Cholesterol | HDL Cholesterol | HMGR |
| Control | 183.0 ± 4.5 | 62.7 ± 2.5 | 99.9 ± 1.9 | 33.8 |
| No. 12 | 125.5 ± 3.0 | 28.4 ± 1.3 | 85.3 ± 1.3 | 14.6 |

TABLE 1-continued

Effects of test compound and tocotrienol on Lipid Metabolism in 6-week old male chickens

| Compound | Total Cholesterol | LDL Cholesterol | HDL Cholesterol | HMGR |
|---|---|---|---|---|
| Tocotrienol | 149.8 ± 4.5 | 42.8 ± 2.8 | 91.7 ± 1.0 | 13.6 |

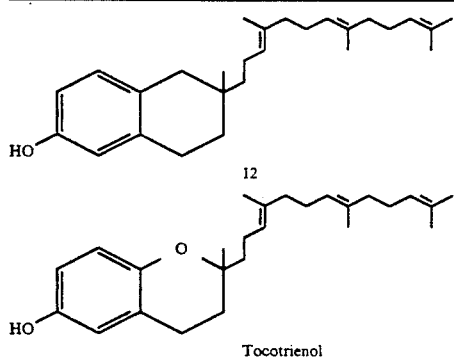

LDL Antioxidant Assay

Whole rabbit plasma was incubated with either vehicle or drug, and the LDL was isolated by ultracentrifugation. EDTA was removed by dialysis and analysis of co-dependent LDL oxidation was determined by conjugated diene formation using the protocol established by Esterbauer et al., (*Free Radical Res. Commun.* 6(1), 75-75 (1989)). The time of the first derivative maximum in the kinetic curves, corresponding to the end of the lag phase (LR) of the reaction, indicates both the intrinsic effectiveness of the antioxidant combined with its local concentration with in the LDL particles. Compound 12 exhibited a LR of 1.32 vs control. Tocotrienol exhibited a LR of 2.01 vs control. This data indicates that test compound 12 exhibits LDL antioxidation properties. However, as expected, compound 12 is less effective in this manner than tocotrienol. Substitution of methylene for oxygen at position 1 would diminish antioxidant capacity.

The results to the above tests demonstrates that the compounds of Formula I and II inhibit HMGR activity which results in a decrease in serum total cholesterol, a decrease in LDL cholesterol levels, and inhibition of LDL oxidation in a manner significantly more efficient than tocotrienol.

Thus, the compounds of Formulas I and II may be readily administered, to treat hypercholesterolemia, hyperlipidemia, and atherosclerosis, and to inhibit LDL oxidation in avian and mammalian systems in need of such treatment. For this purpose, the drug may be administered by conventional routes including, but not limited to, the alimentary canal in the form of oral doses, by injection in sterile parenteral preparations on nasally.

In yet another aspect, the present invention provides a pharmaceutical composition which comprises a compounds of Formulas I and II and a non-toxic pharmaceutically acceptable carrier. These carriers can be solid or liquid such as cornstarch, lactose, sucrose, olive oil or sesame oil. If a solid carrier is used, the dosage forms may be tablets, capsules, powders, troches or lozenges. If the liquid form is used, soft gelatin capsules, syrup or liquid suspensions, emulsions, or solutions in convenient dosage forms may be used. The composition may be made up of any pharmaceutical form appropriate for the desired route of administration. Examples of such compositions include solid compositions for oral administration such as tablets, capsules, pills, powders and granules, liquid compositions for oral administration such as solutions, suspensions; syrups or elixirs and preparations for parenteral administration such as sterile solutions, suspensions or emulsions. They may also be manufactured in the form of sterile solid compositions which can be dissolved in sterile water, physiologically saline or some other sterile injectable medium immediately before use.

The dosage ranges will commonly range from about 50 mg to about 200 mg. Optimal dosages and regimes for a given host can be readily ascertained by those skilled in the art. It will, of course, be appreciated that the actual dose used will vary according to the particular composition formulated, the particular compound used, the disease being treated. Many factors that modify the action of the drug will be taken into account including age, weight, sex, diet, time of administration, route of administration, rate of excretion, condition of the patient, drug combinations, reaction sensitivities and severity of the disease.

All publications cited in this specification are indicative of the level of skill of those skilled in the art to which this invention pertains. Each publication is individually incorporated herein by reference in the location where it is cited.

SCHEME I

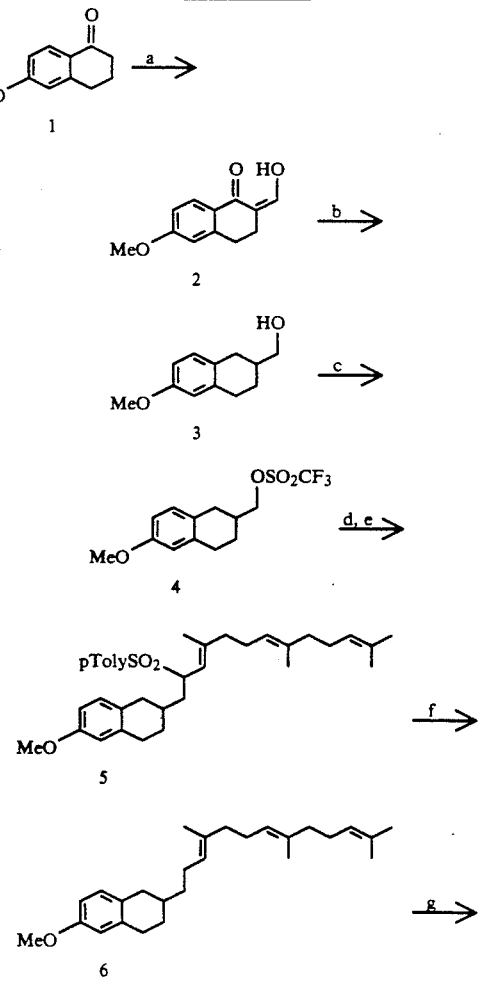

-continued
SCHEME I

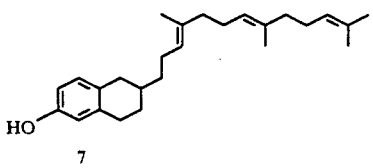

7 a) tBuOK, EtO₂CH, Toluene;
b) tBuNH₂:BH₃, BF₃:Et₂O, CH₂Cl₂;
c) [CF₃SO₂]₂O, Et₃N, CH₂Cl₂;
d) Farnesyl p-Tolysulfone, nBuLi, THF/HMPA;
e) Triflate 4
f) PdCl₂:dppb, LiEt₃BH, THF;
g) p-aminothiophenol, Cs₂CO₃, DMPU,.

SCHEME II

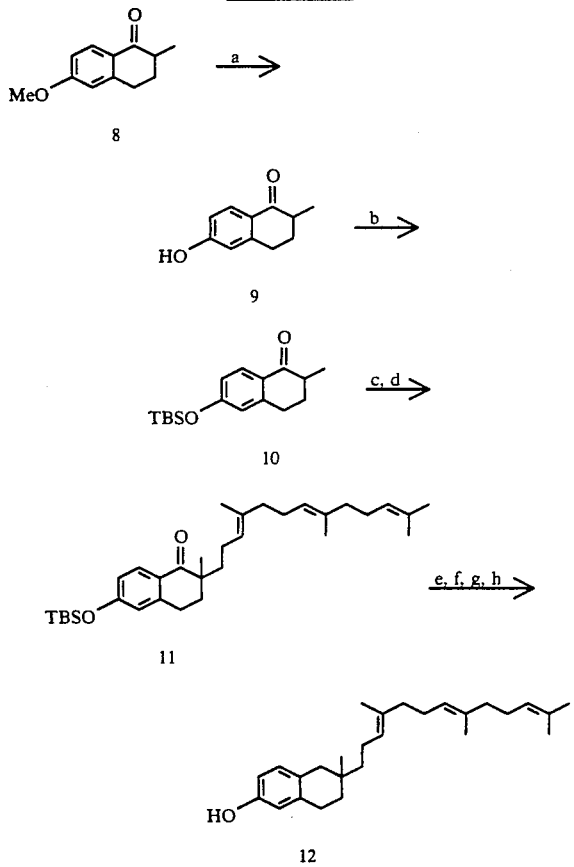

a) Pyridine:HCl, Δ;
b) TBS—Cl, Imidazole, DMF;
c) LDA, THF/HMPA;
d) Homofarnesyl Iodide;
e) LAH, Ether;
f) Ac₂O, Pyridine, CH₂Cl₂;
g) Li, NH₃/THF, NH₄Cl;
h) Tetrabutylammonium Fluoride, Ether.

Chemistry Experimental

The following examples are intended for illustrative purpose only and are not to be construed as limiting the invention in sphere or scope.

All temperatures are understood to be in degrees in C. when not specified. Melting points were recorded on a Thomas-Hoover melting point apparatus and are uncorrected. Boiling points are uncorrected. Infrared spectra were obtained on a Perkin-Elmer Model 1800 FT-IR spectrophotometer. ¹H-NMR spectra were recorded on a Bruker AM 300 spectrometer or a Varian Gemini 300 NMR spectrometer; nuclear magnetic resonance (NMR) spectral characteristics refer to chemical shifts (δ) expressed in parts per million (ppm) with tetramethylsilane (TMS) as an internal standard. The relative area reported for the various shifts in the proton NMR spectral data corresponds to the number of hydrogen atoms of a particular functional type in the molecule. The nature of the shifts as to multiplicity is reported as broad singlets (br s), singlets (s), multiplet (m), doublet (d), triplet (t), or quartet (q). Mass spectra were measured on a Finnegan 4500 spectrometer (low resolution).

Thin-layer chromatography was performed on silica gel 60 F-254 plates purchased from E. Merck and company (visualization with iodine or phosphomolybdic acid); flash chromatography was performed on fine silica (EM Sciences, 230–240 mesh). All reactions were run under dry nitrogen unless otherwise indicated. Dry solvents were purchased from Aldrich, Milwaukee, Wis. in sure/seal bottles and transferred by syringe under nitrogen. Most commercially available starting materials did not require further purification.

EXAMPLE 1

2-Hydroxymethylene-6-Methoxy-1-Tetralone (2)

A mixture of 6-methoxy-1-tetralone (1) (20 g, 0.113 mole) and ethyl formate (16.82 g, 0.23 mole) were dissolved in about 250 mL of toluene. The solution was cooled to about −78° C. under nitrogen and mechanically stirred while potassium t-butoxide (25.5 g, 0.23 mole) was added in portions giving rise to a reddish colored solution. The mixture was slowly warmed to about −5° over a period of about one hour at which time TLC analysis (1:1 EtOAc:Hexanes) indicated a complete conversion to the less polar product. The reaction mixture was quenched with about 10% HCl and extracted with ether. The ether extracts were dried (brine, MgSO₄) and concentrated in vacuo to yield 24.4 g of a dark brown oil. The oil was purified by distillation in a Kugelrohr oven [bath temp. 160°–180°/0.1 mm Hg] to yield the title compound as a yellow oil (22.6 g, 0.11 mole, 98% yield) that solidified on standing [mp 66°–68°, (Lit. Kieboom et al., Synthesis, 476–478, (1970)), mp 68°–69°].

EXAMPLE 2

1,2,3,4-Tetrahydro-6-Methoxy-2-Naphthalenemethanol (3)

2-Hydroxymethylene-6-methoxy-1-tetralone (2) (4.81 g, 0.024 mole) and borane:t-butylamine complex (10.25 g, 0.12 mole) were dissolved in about 250 mL of methylene chloride and the solution was cooled to about −78°. Boron trifluoride etherate (14.5 mL, 0.12 mole) was added dropwise and the mixture was stirred for about 1 hour then warmed to about 23° and stirred for an additional 2 hours. The reaction mixture was quenched with about 1N HCl and extracted with methylene chloride. The methylene chloride extracts were dried (MgSO₄) and concentrated in vacuo. The crude oil was purified by flash chromatography [gradient 3:1 to 1:2 Hexanes:Ether] to yield the title compound as a light yellow oil (3.41 g, 0.018 mole, 75% yield): IR (Film) 3362, 2996, 2918, 1610, 1504, 1464, 1264, 1234, 1040 cm⁻¹; ¹H NMR (CDCl₃) δ1.40 (m, 1H), 1.47 (s, 1H), 1.95 (m, 2H), 1.39,1.45 (d of d, J=10.6,16.1 Hz, 1H), 2.81 (m, 2H), 3.62 (d, J=6.3 HZ, 2H), 3.77 (s, 3H), 6.62 (d, J=2.6 Hz, 1H), 6.68 (d of d, J=8.4,2.6 Hz, 1H), 6.98 (d, J=8.4 Hz, 1H); MS m/e 193 (MH+).

Anal. Calcd. for $C_{12}H_{16}O_2$:
C, 74.97; H, 8.39.
Found: C, 74.70; H, 8.37.

EXAMPLE 3

1,2,3,4-Tetrahydro-6-Methoxy-2-Naphthalenemethanol Trifluoromethanesulfonate (4)

1,2,3,4-Tetrahydro-6-methoxy-2-naphthalenemethanol (2.0 g, 10.42 mmole) and triethylamine (2.2 mL, 15.6 mmole) were dissolved in about 20 mL of methylene chloride and the solution was cooled to about $-78°$ under nitrogen. Triflic anhydride (2.27 mL, 13.54 mmole) was added dropwise the stirred mixture at about $-78°$. After the addition, the mixture was warmed to about $-5°$, at which time TLC [2:1 hexanes:EtOAc] indicated complete conversion to the less polar triflate ester. The reaction mixture was quenched with about 1N HCl and extracted with methylene chloride. The methylene chloride extracts were dried (MgSO$_4$) and concentrated in vacuo. The crude oil was purified by flash chromatography [5:1 Hexanes:Ether] to yield the title compound as a light yellow oil that solidified on standing [mp 52°-54°](3.15 g, 9.72 mmole, 93% yield). The triflate ester was somewhat unstable; a small sample turned black after several hours at about 23°. The bulk was stored at about $-20°$ and was used without delay in the next step: $^1$H NMR (CDCl$_3$) δ1.55 (m, 1H), 2.03 (m, 1H), 2.30 (m, 1H), 2.49,2.55 (d of d, J=10,16 Hz, 1H), 2.85 (m, 3H), 3.77 (s, 3H), 4.50 (d, J=6 Hz, 2H), 6.64 (d, J=2 Hz, 1H), 6.71(d of d, J=8,2 Hz, 1H), 7.01 (d, J=8 Hz, 1H).

EXAMPLE 4

6-Methoxy-2-[2-[(4-Methylphenyl)sulfonyl]-4,8,12-Trimethyl-3(E), 7(E), 11-tridecatrienyl]-1,2,3,4-Tetrahydronaphthalene (5)

n-Butyllithium (7.3 mL, 1.6M, 11.66 mmole) was added dropwise to a solution of all trans farnesyl p-tolysulfone (3.85 g, 10.69 mmole) in THF (30 mL), under nitrogen, at about $-78°$. The orange-colored anion was stirred for about 45 minutes at about $-78°$ then HMPA (5 mL) was added, followed by 1,2,3,4-tetrahydro-6-methoxy-2-naphthalenemethanol trifluoromethanesulfonate (3.15 g, 9.72 mmole) as a THF solution (3 mL). The mixture was slowly warmed to about 23° over a period of about 2 hours at which time TLC [2:1 hexanes:EtOAc] indicated complete consumption of the triflate, commensurate with the formation of a spot co-eluting with farnesyl p-tolysulfone. The reaction mixture was poured into water and extracted with ether. The ether extracts were dried (brine, MgSO$_4$) and concentrated in vacuo to give a light oil. Purification of the crude material by flash chromatography [gradient 6:1 to 5:1 Hexanes:Et$_2$O] yielded the title compound as a clear viscous oil (5.62 g, >100%) which contained about 10% farnesyl p-tolysulfone as indicated by PMR. An analytical sample was obtained by crystallization from methanol which yielded white crystals mp 64°-66°: IR (Film) 3444, 2964, 2916, 1610, 1504, 1450, 1298, 1146 cm$^{-1}$; $^1$H NMR (CDCl$_3$) δ1.25 (d, J=1.2 Hz, 2H), 1.20-1.34 (m, 2H), 1.54 (s, 3H), 1.55 (s, 3H), 1.57 (s, 3H), 1.66 (s, 3H), 1.70-2.10 (m, 9H), 2.37-2.47 (m, 1H), 2.46 (s, 3H), 2.60-2.80 (m, 3H), 3.75 (s, 3H), 3.90 (d of t, J=3.0,10.9 Hz, 1H), 4,92-5.0 (m, 3H), 6.57 (d, J=2.6 Hz, 1H), 6.65 (d of d, J=8.4,2.6 Hz, 1H), 6.92 (d, J=8.4 Hz, 1H), 7.29 (d, J=8.0 Hz, 2H), 7.71 (d, J=8.0 Hz, 2); MS m/e 379 (M(—C$_7$H$_7$S$_1$O$_2$)+).

Anal. Calcd. for $C_{34}H_{46}O_3S_1$:
C, 76.36; H, 8.67.
Found: C, 76.63; H, 8.82.

EXAMPLE 5

6-Methoxy-2-(4,8,12-Trimethyl-3(E), 7(E), 11-tridecatrienyl]-1,2,3,4-Tetrahydronaphthalene (6)

6-Methoxy-2-[2-[(4-methylphenyl)sulfonyl]-4,8,12-trimethyl-3(E), 7(E), 11-tridecatrienyl]-1,2,3,4-tetrahydronaphthalene (2.5 g, 4.68 mmole) was dissolved in about 20 mL of THF. Palladium chloride:diphenylphosphinylbutane (141 mg, 0.23 mmole) was added and the heterogeneous mixture was cooled to about $-5°$ under nitrogen. Lithium triethylborohydride (9.4 mL, 1.0M, 9.4 mmole) was added dropwise giving rise to a brown homogeneous solution. The mixture was stirred for about 12 hours at about $-3°$ then poured into water and extracted with ether. The ether extracts were dried (brine, MgSO$_4$) and concentrated in vacuo to give a light oil. Purification of the crude material by flash chromatography [gradient hexanes to 20:1 Hexanes:Et$_2$O] yielded the title compound as a clear oil (1.03 g, 2.71 mmole, 58%). A sample was distilled in a Kugelrohr oven [bath 160°-180°/0.1 mm] for analysis: IR (Film) 2916, 2852, 1612, 1504, 1452, 1266, 1042 cm$^{-1}$; $^1$H NMR (CDCl$_3$) δ1.37 (m, 2H), 1.50-1.70 (m, 3H), 1.58 (s, 6H), 1.62 (s,3H), 1.66 (s, 3H), 1.88-2.10 (m, 10H), 2.20, 2.35 (d of d, J=10.6, 16.4 Hz, 1H), 2.77 (m, 3H), 3.76 (s, 3H), 5.10 (m, 3H), 6.60 (d, J=2.6 Hz, 1H), 6.66 (d of d, J=8.4, 2.6 Hz, 1H), 6.96 (d, J=8.4 Hz, 1H); MS m/e 381 (MH+).

Anal. Calcd. for $C_{27}H_{40}O_1$:
C, 85.20; H, 10.59.
Found: C, 85.27; H, 10.75.

EXAMPLE 6

1,2,3,4-Tetrahydro-2-(4,8,12-Trimethyl-3(E), 7(E), 11-tridecatrienyl)-6-Naphthalenol (7)

6-Methoxy-2-(4,8,12-trimethyl-3(E), 7(E), 11-tridecatrienyl]-1,2,3,4-tetrahydronaphthalene (957 mg, 2.51 mmole), p-aminothiophenol (630 mg, 5.03 mmole), and cesium carbonate (410 mg, 1.26 mmole) were suspended in about 3 mL of 1,3-dimethyl-3,4,5,6-tetrahydro-2(1H)-pyrimidinone [DMPU]. The flask was purged well with nitrogen and the mixture was heated to about 200° for about 3.5 hours. The honey colored mixture was poured into 1N HCl and extracted with ether. The ether extracts were dried (brine, MgSO$_4$) and concentrated in vacuo. Purification of the crude material by flash chromatography [gradient 20:1→10:1 Hexanes:Et$_2$O] yielded the title compound as a clear oil (800 mg, 2.19 mmole, 87%). A sample was distilled in a Kugelrohr oven [bath 180°-200°/0.1 mm] for analysis: IR (Film) 3346, 2916, 2852, 1612, 1502, 1450, 1230, 1150 cm$^{-1}$; $^1$H NMR (CDCl$_3$) δ1.37 (m, 2H), 1.50-1.70 (m, 3H), 1.58 (s, 6H), 1.62 (s, 3H), 1.66 (s, 3H), 1.88-2.10 (m, 10H), 2.30,2.35 (d of d, J=10.6,16.4 Hz, 1H), 2.77 (m, 3H), 4.45 (s, 1H), 5.10 (m, 3H), 6.53 (d, J=2.6 Hz, 1H), 6.57 (d of d, J=8.4,2.6 Hz, 1H), 6.91 (d, J=8.4 Hz, 1H); MS m/e 367 (MH+).

Anal. Calcd. for $C_{26}H_{38}O_1$:
C, 85.19; H, 10.45.
Found: C, 84.98; H, 10.64.

EXAMPLE 7

2-Methyl-6-Methoxy-1-Tetralone (8) A: 2-Benzoyloxymethylene-6-Methoxy-1-Tetralone Benzoyl chloride (11.4 ml, 0.1 mole) was added to a stirred solution of 2-hydroxymethylene-6-methoxy-1-tetralone 2 (10 g, 0.05 mole) in about 60 mL of pyridine at about 0°. After the addition was complete, the mixture was stirred at about 23° for about 2 hours then poured into water. The solid was filtered and washed with water. The pure product was obtained by recrystallization from methanol to yield 2-benzoyloxymethylene-6-methoxy-1-Tetralone (12.1 g, 0.04 mole, 80% yield), mp 128.5°–129.5°, [Lit. Kieboom et al., *Synthesis*, 476–478, (1970), mp 130°–130.5°].

B: 2-Methyl-6-Methoxy-1-Tetralone 2-Benzoyloxymethylene-6-methoxy-1-tetralone (4.6 g, 0.015 mole) was hydrogenated over platinum oxide (160 mg) in isopropyl alcohol (150 mL) at 55 psi in a Parr hydrogenation apparatus. After about 90 minutes hydrogen uptake ceased and the reaction was stopped. The catalyst was removed by filtration and the solvents were removed in vacuo. The title compound (2.0 g, 0.011 mole, 70% yield) was obtained after purification by flash chromatography [gradient 10:1 to 5:1 EtOAc:Hexanes].

EXAMPLE 8

2-Methyl-6-Hydroxy-1-Tetralone (9)

2-Methyl-6-Methoxy-1-Tetralone (19 g, 0.1 mole) and pyridine hydrochloride (53.1 g, 0.46 mole) were heated neet, under a nitrogen sweep at about 220° for about 2 hours. The melt was cooled, acidified with 1N HCl and dissolved in ethyl acetate. The organic layers were dried (brine, $MgSO_4$) and concentrated in vacuo. Purification by flash chromatography [gradient 7:1 to 5:1 EtOAc:Hexanes] yielded the title compound as a light yellow solid (14.8 g, 0.084 mole, 84% yield), [Lit. Buchta et al., *Ann.* 576, 7–19 (1952)].

EXAMPLE 9

6-Dimethyl-(1,1-Dimethylethyl)silyloxy-2-Methyl-1-Tetralone (10)

2-Methyl-6-hydroxy-1-tetralone (14.5 g, 0.082 mole), t-butyldimethylsilyl chloride (14.9 g, 0.099 mole) and imidazole (14.6 g, 0.21 mole) were dissolved in about 330 mL of DMF. The mixture was allowed to stir at about 23° for about 12 hours. The reaction mixture was poured into water and extracted with ether. The ether extracts were dried (brine, $MgSO_4$) and concentrated in vacuo to give a light brown oil. Purification of the crude material by flash chromatography [10:1 Hexanes:EtOAc] yielded the title compound as a light yellow oil (23.2 g, 0.08 mole, 97% yield): $^1H$ NMR ($CDCl_3$) δ0.22 (s, 6H), 0.97 (s, 9H), 1.23 (d, J=6.8 Hz, 3H), 1.85 (m, 1H), 2.15 (m, 1H), 2.52 (m, 1H), 2.90 (m, 2H), 6.62 (d, J=2.3 Hz, 1H), 6.72 (d of d, J=2.3, 8.6 Hz, 1H), 7.94 (d, J=8.6 Hz, 1H); MS m/e 291 (MH+).

EXAMPLE 10

3,4-Dihydro-6-(1,1-Dimethylethyl) silyloxy-2-Methyl-2-(4,8,12-Trimethyl-3(E), 7(E), 11-tridecatrienyl)-1(2H)-Naphthalenone (11)

Lithium diisopropylamide (24 mL, 1.5M, 0.036 mole) was added to about 25 mL of dry THF under nitrogen at about −78°. 6-Dimethyl-(1,1-dimethylethyl)silyloxy-2-methyl-1-tetralone (6.96 g, 0.024 mole) was added to the LDA solution as a THF solution (15 mL). The mixture was stirred at about −78° for about 2 hours at which time about 5 mL of DMPU followed by homofarnesyl iodide (8.3 g, 0.024 mole) were added. The mixture was stirred at about −3° for about 12 hours then warmed to about 23° and stirred for an additional 24 hours. The reaction mixture was quenched with about 1N HCl and extracted with ether. The ether extracts were dried (brine, $MgSO_4$) and concentrated in vacuo to give a dark brown oil. The oil was purified by flash chromatography [50:1 $Et_2O$:Hexanes] to yield the title compound as a light yellow oil (1.8 g, 0.004 mole, 15% yield): $^1H$ NMR ($CDCl_3$) δ0.22 (s, 6H), 0.97 (s, 9H), 1.18 (s, 3H), 1.45–1.69 (m, 4H), 1.56 (s, 6H), 1.58 (s, 3H), 1.66 (s, 3H), 1.85–2.11 (m, 10H), 2.88 (m, 2H), 5.07 (m, 3H), 6.60 (d, J=2.1 Hz, 1H), 6.72 (d of d, J=2.1,8.6 Hz, 1H), 7.94 (d, J=8.6 Hz, 1H); MS m/e 509 (MH+).

EXAMPLE 11

5,6,7,8-Tetrahydro-6-Methyl-6-(4,8,12-Trimethyl-3(E), (7E), 11-tridecatrienyl)-2-Naphthalenol (12)

A: 2-(1,1-Dimethylethyl)silyloxy-6-Methyl-6-(4,8,12-Trimethyl-3(E), 7(E), 11-tridecatrienyl-5,6,7,8-Tetrahydronaphthalene 3,4-Dihydro-6-(1,1-dimethylethyl)silyloxy-2-methyl-2-(4,8,12-trimethyl-3(E), 7(E), 11-tridecatrienyl)-1-(2H)-naphthalenone (1.8 g, 3.5 mmole) was added as an ether solution (5 mL) to a suspension of lithium aluminum hydride (133 mg, 3.5 mmole) in about 75 mL of ether at about −78°. The mixture was stirred for about 1 hour at about −78° then warmed to about −5° at which time TLC [10:1 Hexanes:Ether] indicated complete conversion to the more polar alcohol. The reaction was quenched at about −5° with saturated sodium sulfate solution, poured into about 1N HCl and extracted with ether. The ether extracts were dried (brine, $MgSO_4$) and concentrated in vacuo to give a light brown oil which was used directly in the next step.

A mixture of the above alcohol (1.4 g, 2.7 mmole), dimethylaminopyridine (33 mg, 0.27 mmole), triethylamine (416 mg, 4.1 mmole), and acetic anhydride (308 mg, 3.0 mmole) were dissolved in about 15 mL of methylene chloride and stirred at about 23° for about 12 hours at which time TLC [10:1 Hexanes:Ether] indicated complete conversion to the acetate ester. The organic fractions were washed successively with about 1N HCl and saturated $NaHCO_3$ solutions then dried ($MgSO_4$) and concentrated in vacuo to give a light brown oil (1.5 g): $^1H$ NMR ($CDCl_3$) δ0.18 (s, 6H), 0.96 (s, 9H), 0.87, 0.96? (s, 3H) [diastereomeric methyl signals], 1.45–1.69 (m, 4H), 1.58 (s, 9H), 1.66 (s, 3H), 1.85–2.11 (m, 10H), 2.03, 2.05 (s, 3H)[diastereomeric acetoxy signals], 2.67 (m, 2H), 5.07 (m, 3H), 5.68, 5.70 (s, 1H)[diastereomeric benzylic methine signals] 6.56 (m, 1H), 6.60 (m, 1H), 7.09, 7.16 (d of d, J=8.6 Hz, 1H) [diastereomeric aryl signals]; MS m/e 493 (M-[$C_2H_3O_2$]+).

To a 1:1 mixture of ammonia/THF (30 mL) at reflux temperature was added lithium metal (5.7 mg, 8.1 mmole) followed by the acetate above (1.5 g, 2.7 mmole) as a THF solution (3 mL). Solid ammonium chloride (1.6 g, mortar ground) was added to the solution and the cooling bath was removed. The reaction mixture was poured into water and extracted with ether. The ether extracts were dried (brine, $MgSO_4$) and concentrated in vacuo to give a light oil. Purification of the crude material by flash chromatography

[20:1 Hexanes:Et₂O] yielded 2-(1,1-Dimethylethyl) silyloxy-6-Methyl-6-(4,8,12-Trimethyl-3(E), 7(E), 11-tridecatrienyl)-5,6,7,8-Tetrahydronaphthalene as a light oil (1.0 g, 2.0 mmole, 57% overall yield).

B: 5,6,7,8-Tetrahydro-6-Methyl-6-(4,8,12-Trimethyl-3(E), 7(E), 11-tridecatrienyl)-2-Naphthalenol 2-(1,1-Dimethylethyl)silyloxy-6-methyl-6-(4,8,12-trimethyl-3(E), 7(E), 11-tridecatrienyl)-5,6,7,8-tetrahydronaphthalene (0.1 g, 2.0 mmole) was dissolved in about 5 mL of ether. The solution was cooled to about −5° and tetrabutylammonium fluoride (2.2 mL, 1M, 2.2 mmole) was added. The mixture was allowed to warm to about 23° and stirred for an additional 10 minutes. The reaction mixture was poured into water and extracted with ether. The ether extracts were dried (brine, MgSO₄) and concentrated in vacuo to give a light oil. Purification of the crude material by flash chromatography [20:1 Hexanes:Et₂O] yielded the title compound as a clear oil (700 mg, 1.84 mmole, 92%): IR (Film) 3344, 2964, 2916, 1612, 1502, 1448, 1218, 1104 cm⁻¹; ¹H NMR (CDCl₃) δ0.93 (s, 3H), 1.20–1.34 (m, 2H), 1.50–1.70 (m, 2H), 1.59 (s, 9H), 1.67 (s, 3H), 1.88–2.10 (m, 10H), 2.45 (AB q, J=16.8 Hz, 2H), 2.72 (t, J=6.8 Hz, 2H), 4.46 (s, 1H), 5.10 (m, 3H), 6.56 (s, 1H), 6.57 (d, J=8.0 Hz, 1H), 6.88 (d, J=8.0 Hz, 1H); MS m/e 381 (MH⁺).

Anal. Calcd. for C₂₇H₄₀O₁:

C, 85.20; H, 10.59.

Found: C, 84.89; H, 10.81.

We claim:

1. The compound having the structural formula

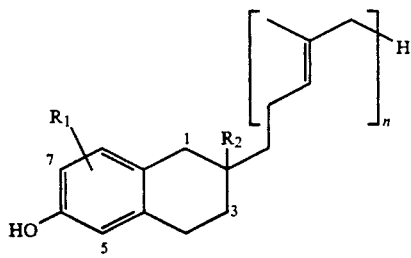

wherein

R₁ represents hydrogen, C₁–C₁₀ alkyl, halogen, or OMe;

R₂ represents hydrogen, C₁–C₁₀ alkyl; and n is 1–3, or pharmaceutically acceptable acid additional salts, metal salts, or solvates thereof.

2. The compound of claim 1 which is the racemic mixture at the C-2 position.

3. The compound of claim 1 which is the R-isomer at the C-2 position.

4. The compound of claim 1 which is the S-isomer at the C-2 position.

5. The compound of claim 1 which is 1,2,3,4-tetrahydro-2-(4,8,12-trimethyl-3(E), 7(E), 11-tridecatrienyl)-6-naphthalenol.

6. The compound of claim 1 which is 5,6,7,8-tetrahydro-6-methyl-6-(4,8,12-trimethyl-3(E), (7E), 11-tridecatrienyl-2-naphthalenol.

7. A pharmaceutical composition for treating or preventing hypercholesterolemia which comprises an effective amount of at least one compound of claim 1, or salt, hydrate or solvate thereof, in combination with a pharmaceutical acceptable carrier or diluent.

8. A pharmaceutical composition for treating or preventing hyperlipidemia which comprises an effective amount of at least one compound of claim 1, or salt, hydrate or solvate thereof, in combination with a pharmaceutical acceptable carrier or diluent.

9. A pharmaceutical composition for treating or preventing LDL oxidation which comprises an effective amount of at least one compound of claim 1, or salt, hydrate or solvate thereof, in combination with a pharmaceutical acceptable carrier or diluent.

* * * * *